United States Patent [19]
Chung

[11] Patent Number: 6,113,620
[45] Date of Patent: Sep. 5, 2000

[54] MAGNETIC NEEDLE FOR ACUPUNCTURE

[75] Inventor: Joong Suck Chung, Seoul, Rep. of Korea

[73] Assignee: Il Yang Pharm. Co., Ltd., Seoul, Rep. of Korea

[21] Appl. No.: 09/202,240

[22] PCT Filed: Jul. 12, 1997

[86] PCT No.: PCT/KR97/00140

§ 371 Date: Apr. 8, 1999

§ 102(e) Date: Apr. 8, 1999

[87] PCT Pub. No.: WO98/02128

PCT Pub. Date: Jan. 22, 1998

[30] Foreign Application Priority Data

Jul. 12, 1996 [KR] Rep. of Korea ............... 96-28114
Oct. 4, 1996 [KR] Rep. of Korea ............... 96-43871

[51] Int. Cl.⁷ .................................................. A61B 17/34
[52] U.S. Cl. ................................... 606/189; 606/201
[58] Field of Search .............................. 606/201, 204, 606/188–189

[56] References Cited

U.S. PATENT DOCUMENTS

| | | | |
|---|---|---|---|
| 3,590,821 | 7/1971 | Orlandini et al. | 128/329 |
| 4,386,506 | 6/1983 | Stump | 63/13 |
| 4,479,495 | 10/1984 | Isaacson | 128/327 |
| 5,135,466 | 8/1992 | Fedorov et al. | 600/11 |
| 5,226,020 | 7/1993 | Li et al. | 600/15 |
| 5,250,067 | 10/1993 | Gelfer et al. | 606/201 |
| 5,741,291 | 4/1998 | Yoo | 606/189 |
| 5,792,171 | 8/1998 | Burdenko et al. | 606/189 |
| 5,904,700 | 5/1999 | Guo | 606/189 |

*Primary Examiner*—Michael Buiz
*Assistant Examiner*—Jonathan D. Goldberg
*Attorney, Agent, or Firm*—R. Neil Sudol; Henry D. Coleman

[57] ABSTRACT

A magnetic needle for acupuncture is disclosed. The magnetic needle of this invention has a housing having an opening and a magnet seated in the opening of the housing. A wedge-shaped projection is held in the opening of the housing so as to project into the exterior of the bottom wall of the housing and come into contact with the magnet. The projection forms an intensive magnetic field around a meridian point having fine electric current or electromagnetic waves. The projection thus magnetically stimulates the meridian point while performing a magnetic massage effect on the meridian point. The magnetic needle accomplishes an acupuncturing effect for relieving pain and curing disease as expected in typical acupuncture.

13 Claims, 6 Drawing Sheets

MAGNETIC NEEDLE FOR ACUPUNCTURE

BACKGROUND OF THE INVENTION

1. Field of the Invention

The present invention relates, in general, to instruments for acupuncture and, more particularly, to a magnetic needle for acupuncture, with a magnetically concentrated wedge-shaped projection being capable of forming an intensive magnetic field around a human meridian point and giving a soft, stable and steady magnetic stimulus to the meridian point thus accomplishing a desirable acupuncturing effect, additionally being capable of performing finger-pressure treatment, improving the acupuncturing effect.

2. Description of the Prior Art

In the Chinese medical art, acupuncture is a treatment for pain and illness in which thin needles are positioned just under the surface of the skin at special nerve centers around the body. In acupuncture, the special nerve centers are called meridian points, which are specifically distributed on both the twelve main meridians and the eight extra meridians at 365 positions.

Modern acupuncture finds that the meridian points interact with nerves, thus forming an electric induction system around the body. Therefore, the acupuncturing effect which can be expected by directly puncturing the meridian points with such thin needles may be achieved by giving electric stimuli to the meridian points while detecting fine electric current or electromagnetic waves formed in the meridian points.

The application of magnetic force for the promotion of health has been actively studied recently. Particularly, the magnetic force is known to preferably promote blood circulation in the body and perform thermotherapeutic effect. In accordance with progress in modern medical science, it is noted that hemoglobin in blood actively reacts with magnetic force and the magnetic poles of the micro particles of the body react with the magnetic field thus performing a magnetic massage effect on the body.

SUMMARY OF THE INVENTION

It is an object of the present invention to attempt to alleviate the above problems occurring in the prior art, and/or to provide a magnetic needle for acupuncture which has a magnetically concentrated wedge-shaped projection being capable of forming an intensive magnetic field around a meridian point and giving a soft, stable and steady magnetic stimulus to the meridian point thus performing a desirable acupuncturing effect, additionally being capable of performing finger-pressure treatment, improving the acupuncturing effect.

Another object of the present invention is to provide a magnetic needle for acupuncture which is detachably attached, by an adhesive fabric, to the surface of the skin around a meridian point with the magnetically concentrated projection being positioned on the meridian point, thus being repeatedly and effectively used for a lengthy period of time.

According to the present invention there is provided a magnetic needle for acupuncture, comprising: a housing having an opening; a magnet seated in the opening of the housing; and a wedge-shaped projection held in the opening of the housing so as to project into the exterior of the bottom wall of the housing and come into contact with the magnet, the projection being adapted for pressing a meridian point and giving finger-pressure effect to the meridian point while forming a magnetic field around the meridian point with the magnetic force of the magnet being concentrated at the tip of the projection.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE PREFERRED EMBODIMENT

Figure 1:
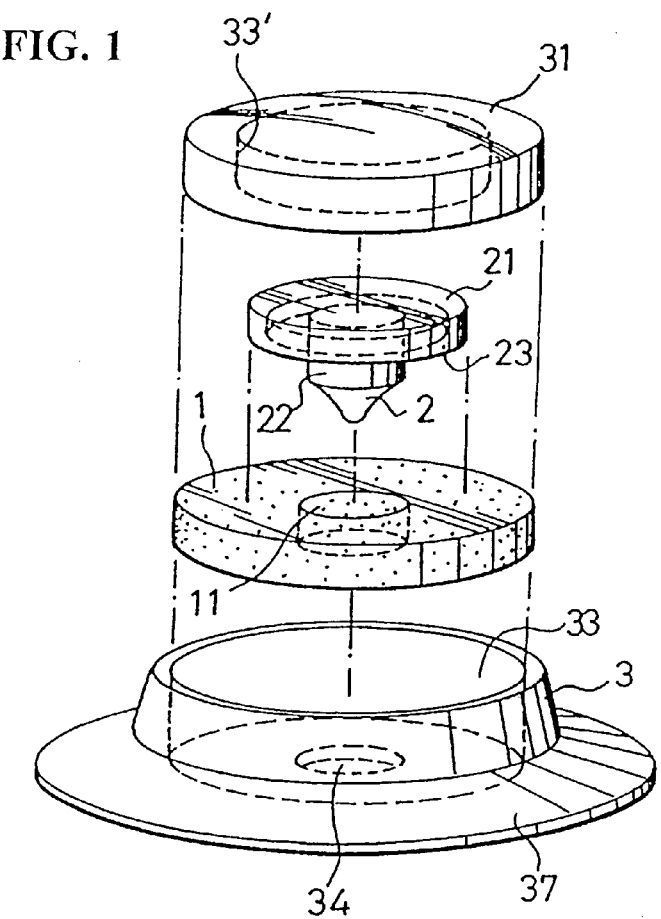
FIG. 1 is an exploded perspective view of a magnetic needle for acupuncture in accordance with the primary embodiment of the present invention.
Figure 2:
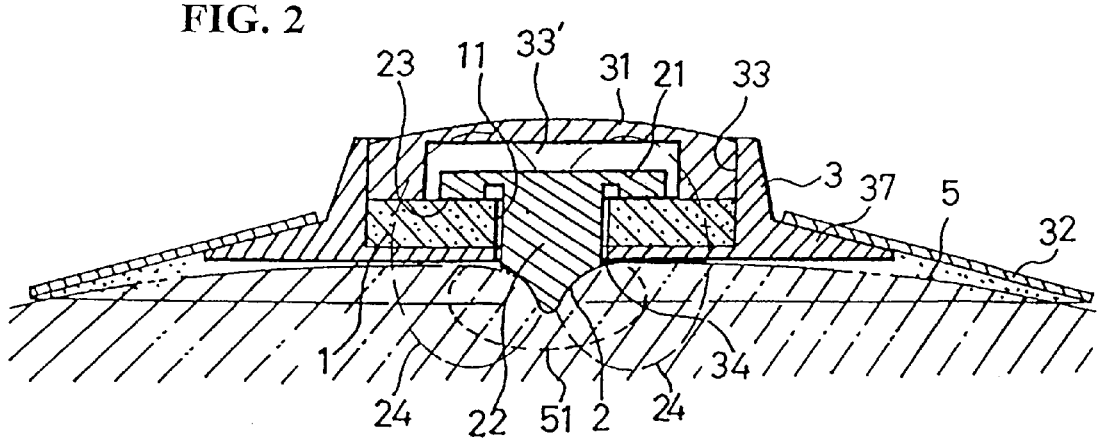
FIG. 2 is a sectional view of the assembled magnetic needle of FIG. 1.

FIGS. 1 and 2 show a magnetic needle for acupuncture in accordance with the primary embodiment of this invention. As shown in the drawings, the magnetic needle of this invention is comprised of a disc-shaped magnet 1 and a magnetically concentrated wedge-shaped projection 2, which are set in a housing 3. The projection 2 forms a magnetic field around a meridian point 51 with the magnetic force of the magnet 1 and gives finger-pressure effect to the meridian point 51.

In consideration of the size of each meridian point 51, the housing 3 is shaped into a caldron configuration with an outer diameter of 10–30 mm and a thickness of 4–10 mm. The housing 3 has a central opening 33, which is bottomed by a centrally holed bottom wall in which the magnet 1 with a central hole 11 is seated. The projection 2 is formed at the lower end of a shaft 22, which passes through both the hole 11 of the magnet 1 and the bottom hole 34 of the housing 3 with the lower end or the projection 2 projecting into the exterior of the bottom wall of the housing 3. The projection 2 is elastically biased downward by an elastic biasing means thus elastically pressing the meridian point 51. In the primary embodiment, the elastic biasing means for the projection 2 is a disc 21, which is coaxially integrated with the top end of the shaft 22 and is seated on the magnet 1 inside the opening 33. The disc 21 has a magnetically attracted surface 23, at which the disc 21 is magnetically and strongly attached to the top surface of the magnet 1. The magnetic force of the magnet 1 is induced to the projection 2 through both the disc 21 and the shaft 22 thus being concentrated at the tip of the projection 2. The magnetic attraction of the magnet 1 to the disc 21 allows the projection 2 to elastically press the meridian point 51. The magnetic attraction force between the magnet 1 and the disc 21 may be adjusted by enlarging or reducing the area of the magnetically attracted surface 23 of the disc 21. After the magnet 1 and the projection 2 are seated in the opening 33 of the housing 3, the opening 33 is closed by a circular lid 31, which is fitted into the opening 33 while forming a cavity 33' inside the opening 33 at a position between the lid 31 and the disc 21.

The projection 2, disc 21 and shaft 22 are all made of magnetizable iron that is capable of becoming magnetized by the magnet 1. It is preferable to coat each of the iron members or the projection 2, disc 21 and shaft 22 with a synthetic resin, gold, platinum, silver or copper layer which effectively prevents the iron members from rusting and has an affinity to the skin.

When the disc 21 is magnetically attracted to the magnet 1 and induces the magnetic force of the magnet 1 to the projection 2 thus causing the projection 2 to become magnetized, the magnetic polarity of the projection 2 is equal to that of the top surface of the magnet 1. When the projection 2 becomes magnetized by the magnet 1 as described above, the magnetic force is concentrated at the tip of the projection 2.

In the present invention, it is preferable to select the magnet 1 from magnets individually having a magnetic flux density of 500–10,000 mm Gauss.

The housing 3 is preferably formed of synthetic resin through an injection molding process or formed of nonferrous metal. The housing 3 is provided with a connection part 37 for connecting an adhesive fabric 32 to the housing 3. The adhesive fabric 32 attaches the magnetic needle to the skin 5 at a position around a selected meridian point 51.

In the operation of the above magnetic needle, the magnetically concentrated projection elastically presses a selected meridian point around the body and performs a magnetic massage effect on the meridian point. The projection also forms a magnetic field around the meridian point, having fine electric current or electromagnetic waves, and magnetically stimulates the meridian point, thus accomplishing an acupuncturing effect for relieving pain and curing disease as expected in typical acupuncture.

Figure 3:
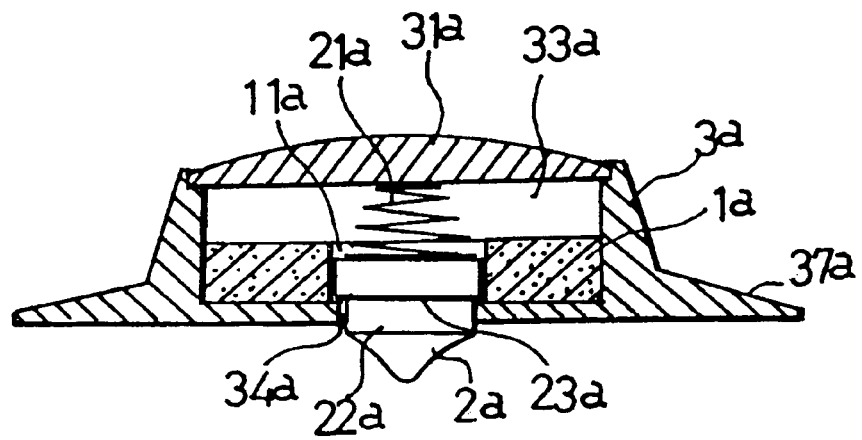
FIG. 3 is a sectional view of an assembled magnetic needle in accordance with the second embodiment of the present invention.
Figure 4:
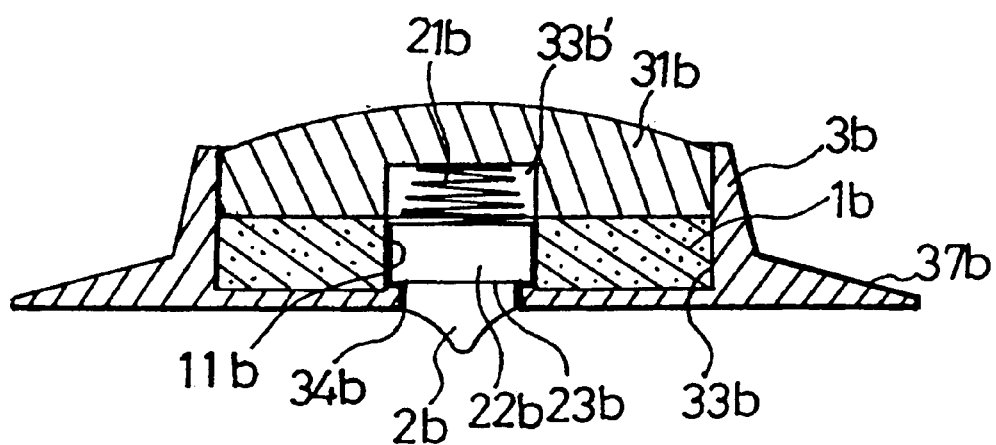
FIG. 4 is a sectional view of an assembled magnetic needle in accordance with the third embodiment of the present invention.

FIGS. 3 and 4 show assembled magnetic needles in accordance with the second and third embodiments of this invention, respectively. In each of the second and third embodiments, the magnetic needle is comprised of a magnet 1a, 1b and a magnetically concentrated projection 2a, 2b, with a compression coil spring 21a, 21b being used as the elastic biasing means for the projection.

In the magnetic needle according to each of the second and third embodiments, the magnet 1a, 1b is seated in the opening 33a, 33b of the housing 3a, 3b. The shaft 22a, 22b, having the projection 2a, 2b at its lower end, passes through the hole 11a, 11b of the magnet 1a, 1b, with the projection 2a, 2b projecting into the exterior of the bottom wall of the housing 3a, 3b. The magnetic force of the magnet 1a, 1b is induced to the projection 2a, 2b through the shaft 22a, 22b, thus causing both the shaft and the projection to become magnetized. The magnetic force is particularly concentrated at the tip of the projection 2a, 2b so that the projection 2a, 2b magnetically and elastically presses a selected meridian point.

The elastic biasing means or the compression coil spring 21a, 21b is installed in the opening 33a, 33b of the housing 3a, 3b covered with the lid 31a, 31b. The spring 21a, 21b biases the shaft 22a, 22b downward. In order to prevent the shaft 22a, 22b from being unexpectedly removed from the housing 3a, 3b, the shaft 22a, 22b is provided with a stop flange 23a, 23b at its top end. The stop flange 23a, 23b is normally stopped by the inside edge of the bottom hole 34a, 34b of the housing 3a, 3b.

In the same manner as described for the primary embodiment, the iron members or the projection 2a, 2b and shaft 22a, 22 b are coated with a synthetic resin, gold, platinum, silver or copper layer.

In addition, the housing 3a, 3b is provided with a connection part 37a, 37b for connecting an adhesive fabric to the housing 3a, 3b.

Figure 5:
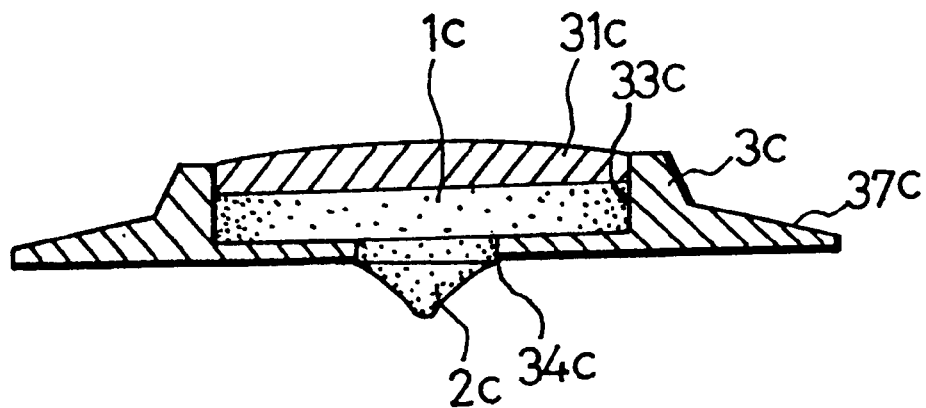
FIG. 5 is a sectional view of an assembled magnetic needle in accordance with the fourth embodiment of the present invention.

FIG. 5 shows an assembled magnetic needle in accordance with the fourth embodiment of this invention. In the fourth embodiment, the magnetic needle is comprised of a magnet 1c and a magnetically concentrated wedge-shaped projection 2c, which are integrated into a single structure. The magnet 1c is seated in the opening 33c of the housing 3c, with the projection 2c of the magnet 1c projecting into the exterior of the bottom hole 34c of the housing 3c and magnetically and elastically pressing a selected meridian point.

In the same manner as described for the primary embodiment, the housing 3c is provided with a connection part 37c for connecting an adhesive fabric to the housing 3c.

In addition, the projection 2c is coated with a synthetic resin, gold, platinum, silver or copper layer.

Figure 6:
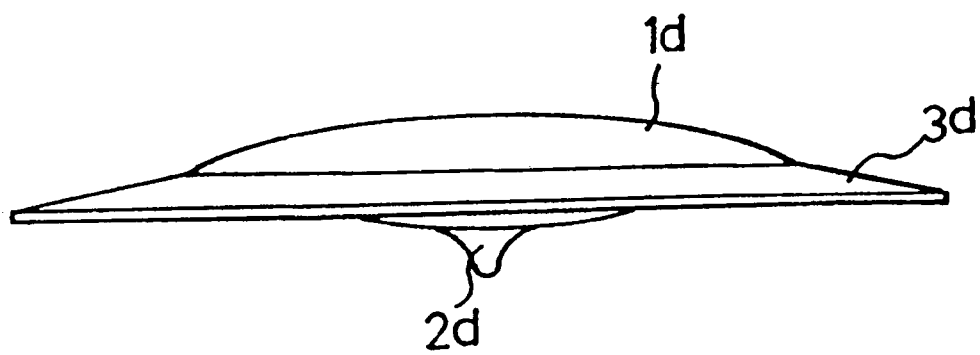
FIG. 6 is a sectional view of an assembled magnetic needle in accordance with the fifth embodiment of the present invention.

FIG. 6 shows an assembled magnetic needle in accordance with the fifth embodiment of this invention. In the fifth embodiment, the housing, the magnet and the magnetically concentrated wedge-shaped projection are integrated into a single structure. The magnet 1d is formed into the configuration of the housing with the wedge-shaped projection 2d being formed at the bottom surface of the magnet 1d. The magnet 1d also has a connection part 3d for connecting an adhesive fabric to the magnet 1d.

The projection 2d is coated with a synthetic resin, gold, platinum, silver or copper layer.

Figure 7:
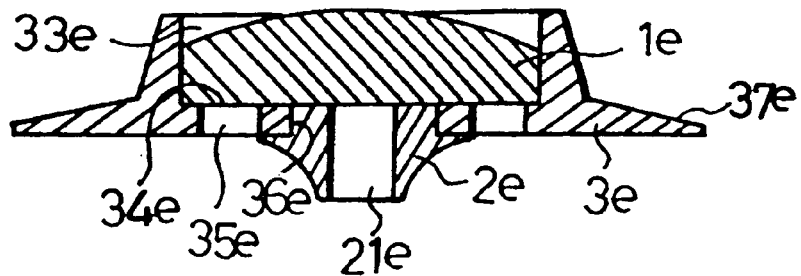
FIG. 7 is a sectional view of an assembled magnetic needle in accordance with the sixth embodiment of the present invention.
Figure 8:
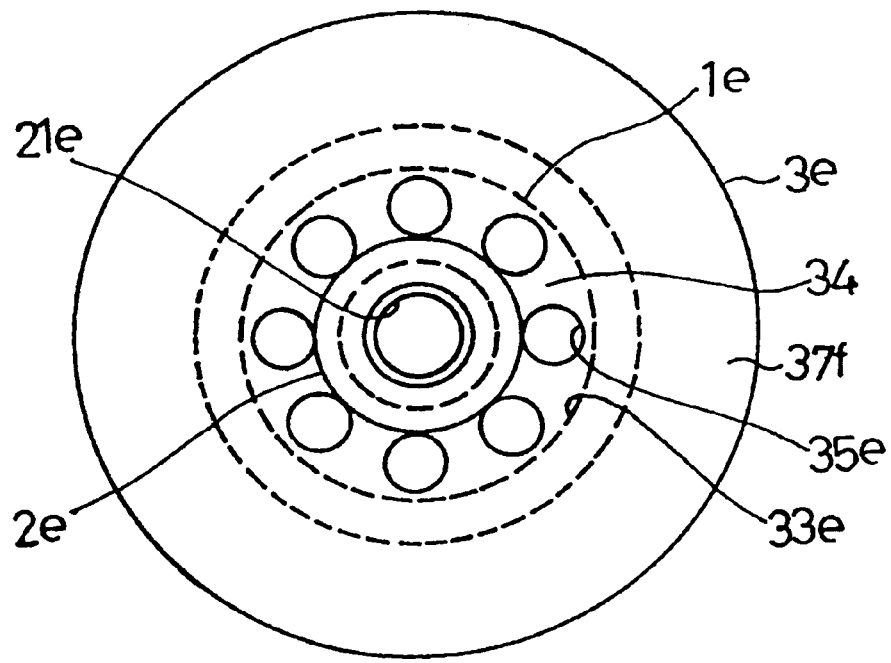
FIG. 8 is a bottom view of the magnetic needle of FIG. 7.

FIGS. 7 and 8 show an assembled magnetic needle in accordance with the sixth embodiment of the present invention. In this embodiment, the magnetic needle is comprised of a magnet 1e and a magnetically concentrated wedge-shaped projection 2e, but a plurality of holes are formed on both the housing 3e and the projection 2e for allowing the skin to breathe.

The magnet 1e is seated in the opening 33e of the housing 3e. Meanwhile, the projection 2e is attached upward to the bottom surface of the magnet 1e through the center hole 36e of the housing's bottom wall 34e, thus allowing the magnetic force of the magnet 1e to be concentrated at the tip of the projection 2e.

In the same manner as described for the primary embodiment, the projection 2e is made of magnetizable iron and is coated with a synthetic resin, gold, platinum, silver or copper layer.

In order to allow the skin to breathe, a plurality of regularly spaced holes 35e are formed on the bottom wall 34e of the housing 3e, while a center hole 21e is axially formed on the projection 2e.

The housing 3e is provided with a connection part 37e for connecting an adhesive fabric to the housing 3e.

Figure 9:
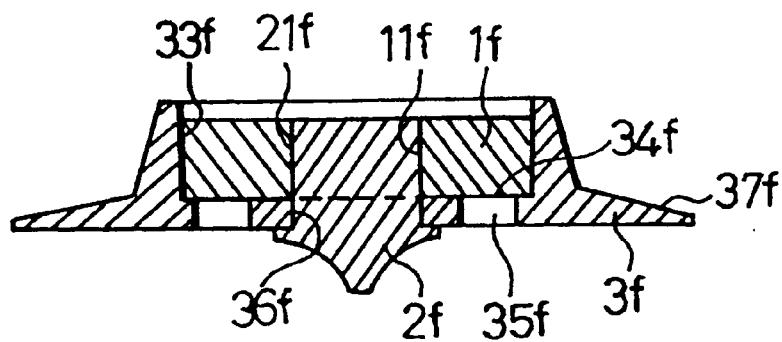
FIG. 9 is a sectional view of an assembled magnetic needle in accordance with the seventh embodiment of the present invention.
Figure 10:
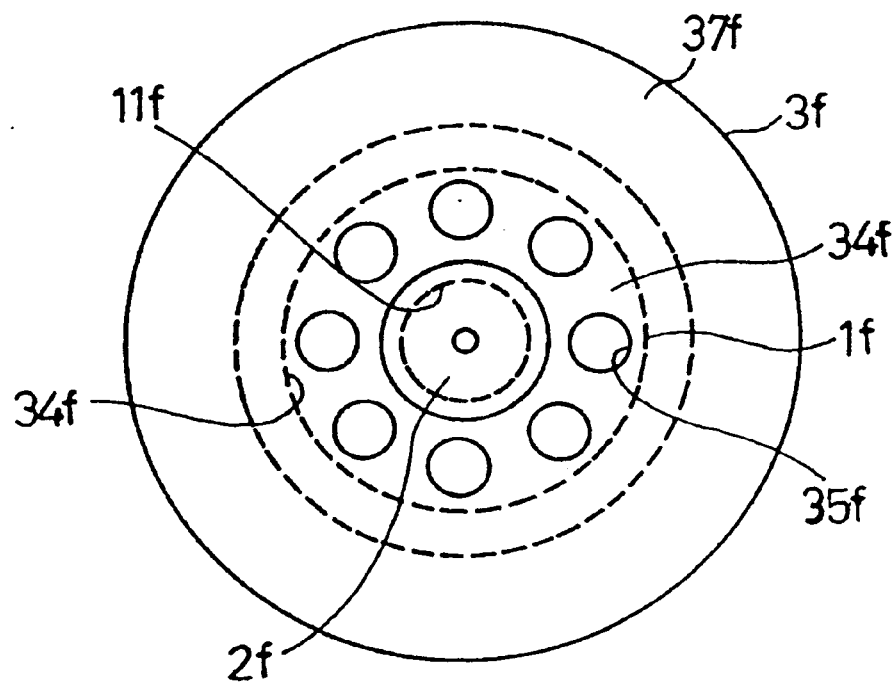
FIG. 10 is a bottom view of the magnetic needle of FIG. 9.

FIGS. 9 and 10 show an assembled magnetic needle in accordance with the seventh embodiment of this invention. In this embodiment, the magnetic needle is comprised of a magnet 1f and a magnetically concentrated wedge-shaped projection 2f, but a plurality of holes are formed on the housing 3f for allowing the skin to breathe.

The magnet 1f is seated in the opening 33f of the housing 3f. Meanwhile, the projection 2f is attached upward to the bottom surface of the magnet 1f through the center hole 36f of the housing's bottom wall 34f, thus allowing the magnetic force of the magnet 1f to be concentrated at the tip of the projection 2f.

In the same manner as described for the primary embodiment, the projection 2f is made of magnetizable iron and is coated with a synthetic resin, gold, platinum, silver or copper layer.

In order to allow the skin to breathe, a plurality of regularly spaced holes 35e are formed on the bottom wall 34e of the housing 3e, while a center hole 21e is axially formed on the projection 2e.

The housing 3e is provided with a connection part 37e for connecting an adhesive fabric to the housing 3e.

FIGS. 9 and 10 show an assembled magnetic needle in accordance with the seventh embodiment of this invention. In this embodiment, the magnetic needle is comprised of a magnet 1f and a magnetically concentrated wedge-shaped projection 2f, but a plurality of holes are formed on the housing 3f for allowing the skin to breathe.

The magnet 1f is seated in the opening 33f of the housing 3f. Meanwhile, the projection 2f is attached upward to the bottom surface of the magnet 1f through the center hole 36f of the housing's bottom wall 34f, thus allowing the magnetic force of the magnet 1f to be concentrated at the tip of the projection 2f.

In the same manner as described for the primary embodiment, the projection 2f is made of magnetizable iron and is coated with a synthetic resin, gold, platinum, silver or copper layer.

In order to allow the skin to breathe, a plurality of regularly spaced holes 35f are formed on the bottom wall 34f of the housing 3f.

The housing 3f is provided with a connection part 37f for connecting an adhesive fabric to the housing 3f.

Figure 11:
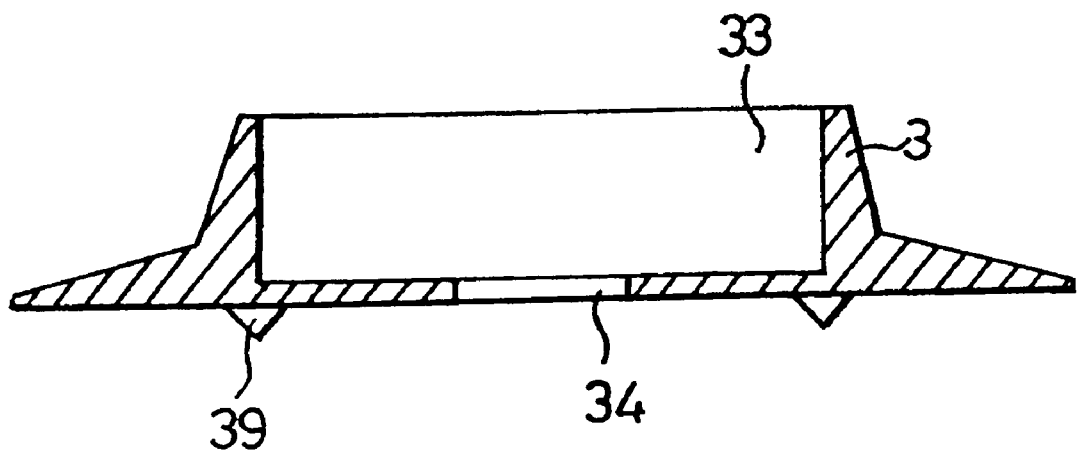
FIG. 11 is a sectional view of a housing with a plurality of pressure projections performing the finger-pressure effect in accordance with another embodiment of the present invention.

FIG. 11 is a sectional view of a housing 3, which is provided with a plurality of pressure projections 39 on the outside bottom surface in accordance with a further embodiment of this invention. The projections 39 perform a finger-pressure effect at a position around a selected meridian point, at which the magnetically concentrated wedge-shaped projection is positioned. The housing 3 of this embodiment may be effectively used with any one of the magnetic needles of FIGS. 1 to 10.

In order to use the magnetic needle for acupuncture of this invention, the magnetic needle is attached to the skin at a position around a selected meridian point using an adhesive fabric. In detailed description, when a plurality of magnetic needles of this invention are attached to the surface of the skin around the meridian points in the same manner as in the typical acupuncturing art, the magnetically concentrated wedge-shaped projection of each magnetic needle forms an intensive magnetic field around each of the meridian points, having fine electric current or electromagnetic waves, and gives a soft, stable and steady magnetic stimulus to each meridian point thus accomplishing an acupuncturing effect for relieving pain and curing disease as expected in typical acupuncture. The wedge-shaped projections also perform finger-pressure treatment, thus improving the acupuncturing effect.

As described above, the present invention provides a magnetic needle for acupuncture. In the magnetic needle of this invention, a magnetically concentrated wedge-shaped projection forms an intensive magnetic field around a meridian point, which has fine electric current or electromagnetic waves. The projection magnetically stimulates the meridian point while performing a magnetic massage effect on the meridian point. The magnetic needle of this invention thus accomplishes an acupuncturing effect for relieving pain and curing disease as expected in typical acupuncture.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A magnetic needle for acupuncture, comprising:
   a housing having an opening and a bottom wall;
   a magnet seated in said opening of the housing;
   a wedge-shaped projection held in said opening of the housing so as to project into the exterior of the bottom wall of said housing and come into contact with the magnet, said wedge-shaped projection being adapted for pressing a meridian point and giving a finger-pressure effect to the meridian point while forming a magnetic field around the meridian point with the magnetic force of the magnet being concentrated at a tip of said wedge-shaped projection, said wedge-shaped projection being formed by a lower end of a shaft passing through a center of said magnet, said wedge-shaped projection being biased by elastic biasing means to elastically press the meridian point, said housing being provided with a connection part for connecting an adhesive web to the housing, said adhesive web being used for attaching the housing to a skin surface.

2. The magnetic needle according to claim 1, wherein said magnet has a magnetic flux density of 500–10,000 Gauss.

3. The magnetic needle according to claim 1, wherein said elastic biasing means comprises:
   a disc integrated with the top end of said shaft and magnetically attracted to the top surface of said magnet thus being attached to the magnet.

4. The magnetic needle according to claim 1, wherein said elastic biasing means comprises:
   a spring received in said opening of the housing to bias the top end of said shaft, with a stop flange being formed on the top end of the shaft and being stopped by the inside edge of a bottom hole of said housing thus preventing the shaft from being removed from the housing.

5. The magnetic needle according to claim 1, wherein said wedge-shaped projection is coated with a layer having an affinity to the skin, said layer being selected from the group of synthetic resin, gold, platinum, silver and copper layers.

6. The magnetic needle according to claim 1, wherein said housing is provided with a pressure projection at its outside bottom surface for performing the finger-pressure effect.

7. The magnetic needle according to claim 1, wherein said housing, magnet and wedge-shaped projection are integrated with each other into a single structure.

8. The magnetic needle according to claim 1, wherein said connection part for connecting said adhesive fabric to the housing includes a flange extending outwardly from said housing.

9. The magnetic needle according to claim 8, wherein said housing has an axis, said wedge-shaped projection extending coaxially with respect to said axis, said flange extending in a plane oriented substantially perpendicularly to said axis.

10. The magnetic needle according to claim 8, wherein said flange is an annular disk-shaped member.

11. The magnetic needle according to claim 1, wherein said adhesive web is a fabric piece.

12. A magnetic needle for acupuncture, comprising:

a housing having a opening and a bottom wall;

a magnet seated in said opening;

a wedge-shaped projection held in said opening, projecting downwardly from said bottom wall of said housing, and disposed in contact with the magnet, said wedge-shaped projection being adapted for pressing a meridian point and giving a finger-pressure effect to the meridian point while forming a magnetic field around the meridian point with the magnetic force of the magnet being concentrated at a tip of said wedge-shaped projection, said wedge-shaped projection being provided with a hole for allowing the skin to breathe.

13. A magnetic needle for acupuncture, comprising:

a housing having a opening and a bottom wall;

a magnet seated in said opening;

a wedge-shaped projection held in said opening, projecting downwardly from said bottom wall of said housing, and disposed in contact with the magnet, said wedge-shaped projection being adapted for pressing a meridian point and giving a finger-pressure effect to the meridian point while forming a magnetic field around the meridian point with the magnetic of the magnet being concentrated at a tip of said wedge-shaped projection, said housing being provided with a hole at its bottom wall for allowing the skin to breathe.

* * * * *